United States Patent
Brewer

(10) Patent No.: US 10,215,721 B2
(45) Date of Patent: Feb. 26, 2019

(54) PRESSURIZABLE DILATOMETER SYSTEM AND APPARATUS

(71) Applicant: David N. Brewer, Solon, OH (US)

(72) Inventor: David N. Brewer, Solon, OH (US)

( * ) Notice: Subject to any disclaimer, the term of this patent is extended or adjusted under 35 U.S.C. 154(b) by 174 days.

(21) Appl. No.: 15/443,598

(22) Filed: Feb. 27, 2017

(65) Prior Publication Data
US 2017/0254764 A1    Sep. 7, 2017

Related U.S. Application Data

(60) Provisional application No. 62/303,411, filed on Mar. 4, 2016.

(51) Int. Cl.
    *G01N 25/16*      (2006.01)

(52) U.S. Cl.
    CPC .................... *G01N 25/16* (2013.01)

(58) Field of Classification Search
None
See application file for complete search history.

(56) References Cited

U.S. PATENT DOCUMENTS

| | | | | |
|---|---|---|---|---|
| 3,182,497 A * | 5/1965 | Rubens | ........ | G01B 13/24 374/55 |
| 3,425,811 A * | 2/1969 | Carignan | ........ | G01N 7/00 374/55 |
| 4,660,412 A * | 4/1987 | Gupta | ........ | G01N 15/088 73/38 |
| 4,739,663 A * | 4/1988 | Peterson | ........ | G01L 9/0091 73/703 |
| 2003/0145894 A1 | 8/2003 | Burns | | |
| 2005/0287673 A1 | 12/2005 | Johhson et al. | | |
| 2007/0260038 A1 | 11/2007 | Ramstack et al. | | |
| 2015/0300867 A1* | 10/2015 | Diaz | ........ | G01N 33/383 73/290 R |

FOREIGN PATENT DOCUMENTS

DE    102005001945 A1 *   8/2005  ........... G01N 9/02
SU    404005 A1 *   10/1973

OTHER PUBLICATIONS

Bernatchez, Pauline, and Dominique Goutier. "Automatic Recording Dilatometer." Review of Scientific Instruments 44, No. 12 (Dec. 1973): 1790-791. doi:10.1063/1.1686059.*
International Search Authority, International Search Report and Written Opinion, dated Jun. 27, 2017, Alexandria, Virginia US.

* cited by examiner

*Primary Examiner* — Clayton E Laballe
*Assistant Examiner* — Leon W Rhodes, Jr.
(74) *Attorney, Agent, or Firm* — Vorys, Sater, Seymour and Pease, LLP; Mark A. Watkins

(57) ABSTRACT

Dilatometer systems for measuring characteristics of material samples are disclosed. In one embodiment, a dilatometer system includes a reactor adapted to receive the test sample, a density trap in fluid communication with the reactor, a first fluid selectively filling the reactor and a portion of the density trap, and a second fluid selectively filling a portion of the density trap. The first fluid and the second fluid are immiscible with one another and selectively form an immiscible fluid boundary in the density trap. The dilatometer system further includes a heater that selectively heats the first fluid.

20 Claims, 4 Drawing Sheets

PRESSURIZABLE DILATOMETER SYSTEM AND APPARATUS

CROSS-REFERENCE TO RELATED APPLICATIONS

This application claims the benefit of U.S. provisional application 62/303,411, filed Mar. 4, 2016.

TECHNICAL FIELD

Various configurations of the current invention relate generally to an apparatus, systems, and methods for measuring changes in volume. More particularly, the apparatus, systems, and methods relate to using a dilatometer for measuring changes in volume. Specifically, the apparatus, systems, and methods provide for a dilatometer that uses a pair of at least two immiscible liquids.

BACKGROUND

Dilatometers are analytical instruments that measure the change in volume of a substance due to thermal, physical or chemical processes. Generally, these instruments employ a variable temperature electric furnace in which the test specimen is heated at a programmed rate to a desired elevated test temperature. Conventionally, the test specimen, which commonly is from about 10 to about 50 mm in length, is held within such furnace between a flat surface on a stationary object and an opposing flat surface on a movable object, such as a ceramic pushrod, that extends outside the furnace. Temperature induced changes in the length of the specimen are transmitted through the rod to a dilation sensor, which can be a mechanical, optical or electrical system for amplifying and measuring the change in position of the rod. Conventional instruments are useful for measuring specimen dilation within the range of from ambient temperature to the maximum temperature of the furnace, which commonly is about 1000 degrees Celsius and often is as high as 1500 degrees Celsius or more.

The least complicated dilatometers in common use are those in which the push rod is coupled to a dial gauge and the dilation of a specimen is read directly from that gauge. Such dial gauge dilatometers are simple to use and inexpensive, but generally are suitable only for low to moderately elevated temperature applications that do not demand high precision. According, dilatometers with improved precision may be desired.

SUMMARY

In one embodiment, a pressurizable dilatometer system may be used to determine a glass transition temperature, as well as other parameters, of a test material. The dilatometer system includes a reactor to receive a test sample, a pump, a density trap, a first fluid line connected between and placing the reactor and the density trap into fluid communication, a second fluid line connected between and placing the pump and the density trap into fluid communication, a first fluid adapted to fill the reactor, the first fluid line and a portion of the density trap. A second fluid fills a reservoir and/or other portions of the pump, the second fluid line and a portion of the density trap. The first and second fluids form an immiscible fluid pair. In other configurations, three or more fluids may be used to create two or more immiscible fluid boundaries. An immiscible fluid boundary is formed where the first and second pair of immiscible fluids meet in the density trap. In one use of the dilatometer system, the pump creates a pressure value on the first and second fluids forming the immiscible fluid pair which in turn creates a similar pressure on and the test sample. A movement of the immiscible fluid boundary is used to determine a change in the system volume. In some embodiments, the first fluid is any liquid metal or metal alloy and the second fluid is a power transferring fluid. For example, the first fluid may be Galinstan® or another liquid metal or metal alloy that is liquid over the range of temperatures of interest.

Another configuration is a pair of immiscible fluids in a pressurizable dilatometer system. The dilatometer system includes a reactor adapted to receive a test sample. A working fluid that is a first fluid of an immiscible fluid pair of fluid is adapted to fill the reactor. A hydraulic fluid that is a second fluid of an immiscible fluid pair is in contact with the first fluid to form an immiscible fluid boundary. A pump is adapted to pump the second fluid to create at least one pressure value on the second fluid, the first fluid, and the test sample. A heater is adapted to heat the first fluid as well as the test sample in the reactor over a range of temperature values. A movement of the immiscible fluid boundary is used to calculate one or more parameters of the test sample including, for example, a glass transition temperature, $T_g$, of the test sample. In some embodiments, the first fluid is a liquid metal or a liquid gallium eutectic alloy, including being Galinstan.

Another configuration is a method of using two different fluids in a dilatometer that form an immiscible fluid pair. The method begins by filling a reactor containing a test sample as well a first fluid line leading at least partially into a density trap with a first fluid. A second fluid is pumped through a second fluid line and at least partially into the density trap so that the first fluid and the second fluid contact each other in the density trap forming an immiscible fluid interface. A desired pressure is applied to the second fluid to pressurize the second fluid, the first fluid, and the test sample. The reactor and test sample are also optionally heated through a range of temperatures. The glass transition temperature is found based, at least in part, on the movement of the immiscible fluid interface in the density trap. In some configurations, the rate of movement of the immiscible interface changes, indicating a rate of change of a specific volume of the test sample, which indicates at what temperature the glass transition temperature, $T_g$, occurs. In some configurations, the first fluid is Galinstan and the second fluid is a fluid that is immiscible with the first fluid and generally incompressible at the working pressures, such that the second fluid may transfer pressure to the first fluid.

BRIEF DESCRIPTION OF THE DRAWINGS

One or more preferred embodiments that illustrate the best mode(s) are set forth in the drawings and in the following description. The appended claims particularly and distinctly point out and set forth embodiments according to the present disclosure.

The accompanying drawings, which are incorporated in and constitute a part of the specification, illustrate various example methods and other example embodiments of various aspects of the disclosure. It will be appreciated that the illustrated element boundaries (e.g., boxes, groups of boxes, or other shapes) in the figures represent one example of the boundaries. One of ordinary skill in the art will appreciate that in some examples, one element may be designed as multiple elements or that multiple elements may be designed as one element. In some examples, an element shown as an internal component of another element may be implemented as an external component and vice versa. Furthermore, elements may not be drawn to scale.

Similar numbers refer to similar parts throughout the drawings.

DETAILED DESCRIPTION

As used herein, "hydraulic fluid" refers to a fluid that is capable of transferring power. In various embodiments, the hydraulic fluid may be generally incompressible at the working temperatures and pressures of the dilatometer system. Examples of such hydraulic fluids include, without limitation, petroleum-based fluids or ionic fluids, for example imidazolium-based ionic liquids.

Figure 1:
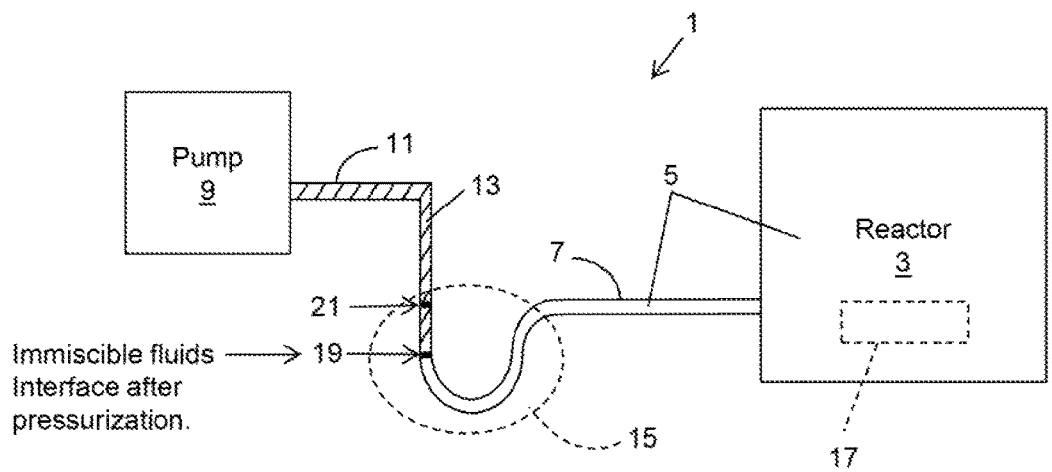
FIG. 1 illustrates an example embodiment of a volumetric dilatometer system according to one or more embodiments.

FIG. 1 illustrates an example embodiment of a pressurizable volumetric dilatometer system 1. One element of this embodiment of the dilatometer system 1 is that the dilatometer system 1 has a larger range of volume change than a conventional system that has its volume change restricted by the range of its bellows. This dilatometer system 1 is a pressurizable, thermally controlled dilatometer that measures volume change in materials, due to physical, thermal or chemical processes. In an exemplary embodiment of FIG. 1 the dilatometer system 1 may be operated at a high pressure (in the range of 20 Ksi) and a high temperature (up to approximately 1000 degrees Celsius) to measure volume change in material samples. However, other embodiments may operate at any other desired pressures and temperatures, limited in part by the thermal capability of the fluid utilized in the system and the additional system components. The pressures and/or temperatures provided herein are representative in nature and shall not be seen as limiting in any way. In this example, the dilatometer system 1 may heat a polymer sample material up to the range of approximately 300 degrees Celsius and then the polymer sample material's glass transition temperature, $T_g$, is determined by measuring changes in volume at temperature and pressure. The dilatometer system 1 includes a reactor 3, a working fluid 5, within the reactor 3 and within a working fluid line 7, a pump 9, a hydraulic line 11, and a hydraulic fluid 13. In a representative embodiment, the working fluid 5 and the hydraulic fluid 13 are an immiscible fluid combination and the final intersection 21 (after being pressurized as discussed below) of the working fluid 5 and the hydraulic fluid 13 is illustrated as labeled in FIG. 1. In general, a density trap 15 is formed in the proximity of where the working fluid line 7 and the hydraulic line 11 intersect, as illustrated. Even though a P-type density trap is illustrated, those of ordinary skill in the art will appreciate that other types of density traps may be used to measure changes in volume of the fluids as further discussed below. In some configurations, the pump 9 may be a programmable high pressure syringe type of pump, but in other embodiments it may be another suitable pump, as determined and/or understood by those of ordinary skill in the art. Suitable pumps may be capable of exerting high pressure with the ability to meter fluid with high precision. In one example, one family of suitable pump for this purpose is the Teledyne Isco Model 30D syringe pumps.

In this exemplary embodiment, the primary components of the dilatometer system 1 such as the reactor 3, the working fluid line 7, the hydraulic line 11, and the pump 9 are made primarily out of rigid materials such as a suitable metal to minimize changes of volume of components of the dilatometer system. In a representative embodiment, stainless steel is used to form many of the components of the dilatometer system as stainless steel has high stiffness and strength, and is minimally reactive with the working fluid 5 or the hydraulic fluid 13. In one embodiment, the reactor or sample cell is sized large enough to accommodate the sample as well as the volume change (increase) that may come from thermal expansion and/or phase transformation. By way of example only, a material specimen that the dilatometer system 1 evaluates may be in the size range of 1 to 2 cubic centimeters. The volume of the sample cell may be approximately twice the sample volume. Other samples may include carbon fiber composites, wood samples, and virtually any other materials deemed usable in the system.

Having introduced the basic components of the example configuration of the dilatometer system 1 of FIG. 1, the concept of glass transition temperature, $T_g$, and other related concepts are explained before the functionality of the dilatometer system 1 is explained. Polymers are generally divided into two classes, thermosets and thermoplastics. Thermoset polymers are formed from resins that are initially in a viscous state. Heating the thermosetting resin cross-links the resin and increases the strength of the polymer. In general, thermoset polymers do not substantially soften upon subsequent application of heat, and therefore thermoset polymers can generally not be re-molded or re-heated after their initial forming and heating. Thermoplastic polymers may be heated, and the polymer becomes more fluid as heat is introduced. When the thermoplastic polymer is maintained at a temperature below its glass transition temperature, $T_g$, the material behaves as a rigid material. As the temperature of the thermoplastic polymer exceeds the $T_g$, the polymer becomes more pliable and fluid-like and loses strength. Forces applied to the thermoplastic polymer below the $T_g$ may result in elastic (recoverable) deformation, while the same forces applied at temperatures above the $T_g$, may result in plastic (non-recoverable) deformation the thermoplastic polymer. Thermoplastic polymers are generally used in products and applications in which the temperature of the thermoplastic polymer is below the material's $T_g$. Accordingly, accurate measurement of the $T_g$ of thermoplastic polymers is desirable for proper selection of materials for a product and its applications.

Figure 2:
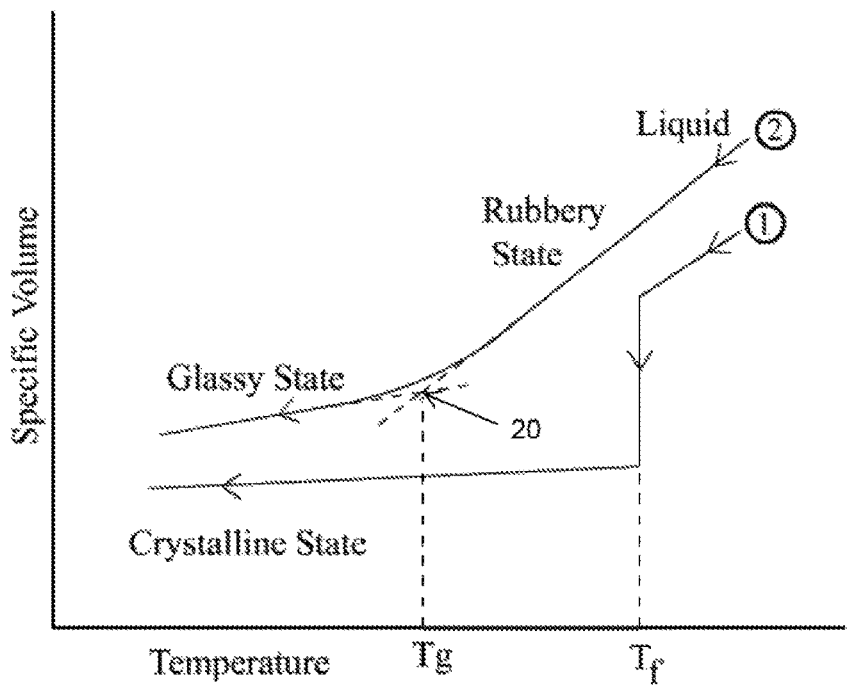
FIG. 2 illustrates an example graph of specific volume vs. temperature and where the glass transition temperature, $T_g$, is found for an amorphous material and where the freezing temperature, $T_f$, is found for a crystalline material.

As illustrated in FIG. 2, when an amorphous material (line (2)) is heated from the glassy state, below the $T_g$, to the rubbery state, above the $T_g$, there is not an abrupt change in volume. Instead, at or around the glass transition temperature, $T_g$, of the material, there is a change in coefficient of thermal expansion. As depicted in FIG. 2, as the material is brought through and above the $T_g$, the slope of the curve of specific volume vs. temperature, moves from a relatively low value in the glassy state to a relatively higher value in the rubbery state. The intersection of the two linear line segments of the amorphous material curve (2) defines the dilatometric $T_g$. A comparison between a crystalline material (1) and an amorphous material (2) is illustrated in FIG. 2. In some configurations, the dilatometer system 1 may be used to identify the freezing temperature, $T_f$, of a crystalline material. The freezing temperature, $T_f$, is similar to the glass transition temperature, $T_g$, of amorphous materials discussed above, as $T_f$ is the temperature at which a crystalline material moves from a crystalline state to an amorphous state, as illustrated by curve (1) in FIG. 2.

In some embodiments, the change in the coefficient of thermal expansion (e.g., the slope change of specific volume vs. temperature) may be measured by evaluating the movement of the immiscible fluid boundary while steadily increasing temperature on the test sample 17 indicates the value of the glass transition temperature, $T_g$, of the test sample.

It is important to note that while the $T_g$ is an parameter that can be determined with a dilatometer, it is not the only parameter that may be determined. The various configurations of a dilatometer disclosed herein may be capable of measuring volume at different temperatures and pressures. As understood by those of ordinary skill in this art, the bulk modulus of a material, compressibility, specific volume, coefficient of thermal expansion, and other properties may also be determined using various configurations of the dilatometers disclosed herein.

In operation and with continued reference to FIG. 1, a sample 17 is placed inside the reactor 3 as illustrated. Next, the reactor 3, the working fluid line 7, and at least a portion of the density trap 15 will be filled with a working fluid 5. In some embodiments, the working fluid may be any metal or metal alloy that is fully liquid at the working temperatures (i.e., the liquidus temperature of the metal or metal alloy is below the lowest working temperature) of the dilatometer system 1. The second fluid is a fluid that is immiscible with the working fluid. For example, the first fluid may liquid Galinstan®, which is a commercially available gallium eutectic alloy available from Geratherm Medical AG. In one example, the second fluid may be a hydraulic fluid. The working fluid 5 and the hydraulic fluid 9 form a system of at least two immiscible liquids. In some embodiments, at least one of the at least two immiscible fluids is an ionic liquid that is prone to oxidation and not miscible in many nonpolar polymers. At the same time or at a close time during the sample testing operation, a hydraulic fluid 13 is pumped by the pump 9 into the hydraulic line 11 and partially into the density trap 15, as illustrated in FIG. 1. Because the pump 9, the hydraulic line 11 the density trap 15, and the reactor 3 are in fluid communication with one another, pressure may equilibrate across the first fluid and the second fluid. However, because the hydraulic fluid 9 and working fluid 5 form a pair of immiscible fluids, they will not mix together and, instead, will form a boundary at the immiscible fluids interface. For example, an immiscible fluid boundary may be formed at point 19 in the density trap 15 (after pressure is added but before heat is added to the system 1), as illustrated in FIG. 1.

Liquid Galinstan, however, typically exhibits low surface tension. This low surface tension corresponds to an increased likelihood that the liquid Galinstan will wet solid surfaces that the liquid Galinstan comes into contact with. Wetting certain surfaces, for example, seals and components of a pump, is undesirable, and may compromise the functionality of certain devices. In contrast, hydraulic fluid may not be inert with the polymeric material being sampled, in particular at elevated temperatures. Accordingly, the dilatometer system 1 of the present disclosure incorporates a combination of immiscible fluids: the first liquid is compatible with the polymeric sample being tested and the second liquid is compatible with those components that direct the flow of fluid to encapsulate and pressurize the first liquid, which surrounds the sample. The boundary between the two immiscible fluids, therefore, becomes an appropriate position to monitor the change in volume of the polymeric sample.

Before a test begins, pump 9 will pump hydraulic fluid 9 into the hydraulic line 11 to pressurize the dilatometer system 1 including reactor 3 to a desired pressure. This may cause the hydraulic fluid/working fluid boundary to be located at position 19 (FIG. 1) on density trap 15 (again after pressure but before heat is added to the system 1). Once the desired pressure is established by reading a pressure gauge or having a computer detect the desired pressure with a sensor, the temperature of the reactor 3 and the sample 17 inside the reactor 3 is increased in order to determine the glass transition temperature, $T_g$. As illustrated in FIG. 2, the specific volume of a polymeric sample 17 will increase as the temperature of the working fluid 5 increases, thereby allowing more working fluid 5 to be pushed into the density trap 15. For example, the boundary of the immiscible fluids (hydraulic fluid 13 and working fluid 5) may move from point 19 (FIG. 1) to point 21 in the density trap 15. The glass transition temperature, $T_g$, is determined when the rate of increase of specific volume increases to a higher slope/rate of increase as the sample enters the rubbery state as indicated by point 20 in FIG. 2. For example, the hydraulic fluid 13 may reach position 21 on the hydraulic line/density trap 15 as illustrated in FIG. 1 as the sample approaches and enters the liquid state. The glass transition temperature, $T_g$, may be calculated based on the position of the immiscible fluid boundary based on the temperature, as depicted in FIG. 2.

It should be noted that pressure of the fluids and heat may affect (expand) the reactor 3, the pump 9, the working fluid line 7, hydraulic line 11, the density trap 15, as well as other components of the dilatometer system 1 that may result in an increased system volume change being recorded. Under ideal test conditions, nothing except the test sample may contract or expand. Thus, the change in volume measured during the test, including thermal expansion, will be the result of the compression/expansion of the pressurizing fluid 13, the working fluid 5, the equipment stiffness and the specimen 17. The dilatometer system 1 may be designed and sized with a factor of safety, which should significantly minimize the elastic contribution from pressurization. Because the combination of fluids (the working fluid 5 and the hydraulic fluid 13) are immiscible, the contribution to the overall volume change will be repeatable and additive. The fluid volume change from pressurization will be the compressibility of the working fluid times the volume of the working fluid plus the compressibility of the pressurizing fluid times the volume of the pressurizing fluid. Further, the volume change of the fluid and the surrounding enclosure caused by temperature and pressure variation may be captured and the data gathered may be calibrated to minimize the introduction of error into the compilation of data. As understood by those of ordinary skill in the art, this can be computed or measured to create a calibration curve for the dilatometer system 1 that can be subtracted from the observed total volumetric changes during the test, resulting in the net volume change due to the specimen 17 to accurately record the specimen's volume change.

In some instances it may be desired to determine $T_g$ for a variety of different pressures. In certain cases, the pump 9 will increase pressure on the hydraulic fluid 13 to a first higher pressure which will in turn increase pressure on the working fluid 5 and the test sample 17. Higher pressure requires more heat to reach the $T_g$. As discussed later with reference to FIG. 3, the heat may be supplied by a heater associated with the reactor 3. Once the new $T_g$ is found at the first higher pressure, the dilatometer system 1 may first be cooled and then the pump 9 may again increase the pressure on the hydraulic fluid 13, which again increases pressure on the working fluid 5 and the test sample 17 to a second higher pressure. Next, the temperature of the reactor 3 is again increased/swept higher until a new higher $T_g$ is found at the new second higher pressure and temperature combination. This can be repeated to find pressure/temperature combinations for as many different $T_g$ values of a sample or material as desired. Similarly, in some circumstances, it may be desirable to decrease pressure. For example, to measure the bulk modulus of a material the temperature may be held constant while pressure and volume change are measured both during loading (increase in pressure) and unloading (decrease in pressure). Comparing these curves would be indicative of sample densification. Also, an operator desiring to run a test maintaining volume constant while changing temperature, would appreciate that the pressure may have to either increase or decrease to maintain the constant volume (isochoric). In general, a user may want to study a sample under isothermal, isobaric, or isochoric conditions.

The dilatometer system 1 may measure many thermodynamic properties in materials. These include $T_g$ (if single phase), 2 $T_g$s (if two phase), crystal melting and cooling temperatures (along with volume change associated with melting or solidification) that would be indicative of a degree of crystallinity. The dilatometer system 1 may also be used to evaluate engineering properties like bulk modulus, which may allow for back-calculating other elastic properties of anisotropic materials, such as films and fibers. The dilatometer system 1 may also used to determine thermoplastic properties of some materials.

Figure 3:
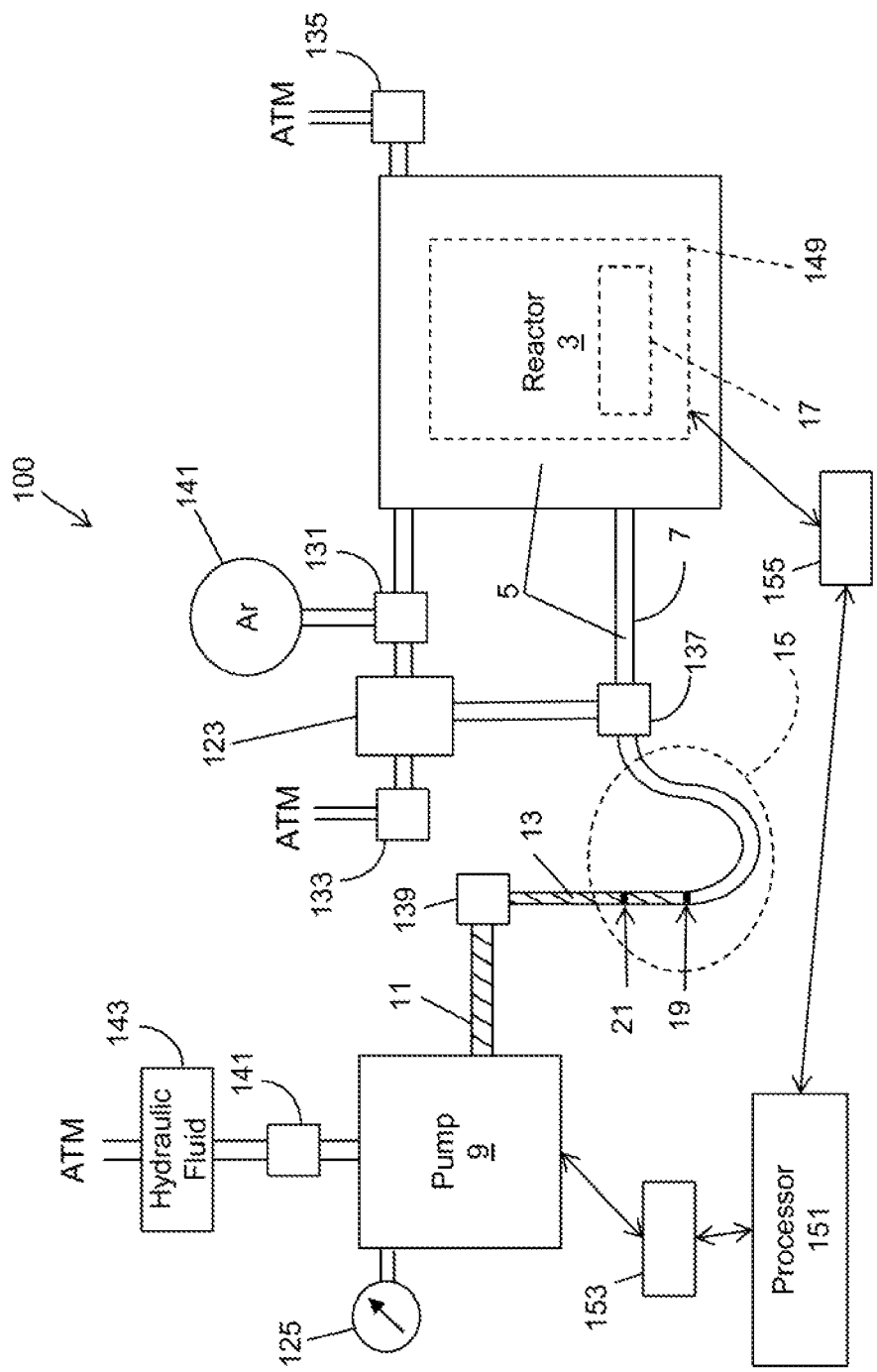
FIG. 3 illustrates another example embodiment of a volumetric dilatometer system according to one or more embodiments.

In further detail, in some conditions, the determination of $T_g$ for polymers has been found to be rate dependent. Thus, FIG. 3 illustrates a pressurizable dilatometer system 100 that utilizes an electronic computer (e.g., processor 151) that is used to control the pump 9 and may be used to add a level of reproducibility that was not previously available in prior art systems, in particular to rate-sensitive material properties. The processor 151 or another microprocessor based controller/logic may also be added to control a heater 149 that is associated with the reactor 3 to provide for controllable heating and cooling rates. In some embodiments, the processor 151 may interface through a pump controller 153 and a heater controller 155 when controlling the pump 9 and heater 149.

"Processor" and "Logic", as used herein, includes but is not limited to hardware, firmware, software and/or combinations of each to perform a function(s) or an action(s), and/or to cause a function or action from another logic, method, and/or system. For example, based on a desired application or needs, logic and/or processor may include a software-controlled microprocessor, discrete logic, an application specific integrated circuit (ASIC), a programmed logic device, a memory device containing instructions or the like. Logic and/or processor may include one or more gates, combinations of gates, or other circuit components. Logic and/or a processor may also be fully embodied as software. In various embodiments, the processor may execute the logic that is stored as a computer readable instruction set that is stored in the memory that is associated with the processor. Where multiple logics and/or processors are described, it may be possible to incorporate the multiple logics and/or processors into one physical logic (or processors). Similarly, where a single logic and/or processor is described, it may be possible to distribute that single logic and/or processor between multiple physical logics and/or processors.

The dilatometer system 100 of FIG. 3 further includes a working fluid tank 123 and an argon tank 141 or a tank with another non-reactive gas. In one configuration, the working fluid 5 is Galinstan, which is a commercially available gallium eutectic. As illustrated, three-port valves 131, 137 connect the working fluid tank 123 and the argon (or another suitable non-reactive gas) tank 141 to the reactor 3. Two-port valves 133, 135 provide a way to connect the reactor 3 and the working fluid tank 23 to atmosphere (ATM). Two-port valves 139 and 141 provide a way to shut off the hydraulic line 11 from the density trap 15 as well as a way to shut off the pump 9 from a hydraulic fluid tank 143. The pump 9 contains a pressure gauge or another suitable pressure measurement device 125 to indicate a pressure in the pump 9 and the dilatometer system 100. The dilatometer system 100 of FIG. 3 has many similar components of the system 1 of FIG. 1. Similar components include a reactor, 3, a working fluid 5, within the reactor 3 and within a working fluid line 7, a pump 9, a hydraulic line 11, and a hydraulic fluid 13. An end of the working fluid line 7 and the hydraulic line 11 form a density trap 15 in the form of a P-trap, as illustrated. Of course, in other embodiments, other types of density traps may be used.

In preparation for a test, the valve 131 connected to the argon tank 141 can be opened to allow argon to push working fluid 5 from the working fluid tank 123 into the reactor 3 as well as the working fluid line 7 and to the density trap 15. Valve 135 is opened to allow air or other gasses in the reactor 3 to vent to the atmosphere when the working fluid 5 is being filled into the reactor 3. Valve 141 and valve 139 are both opened to allow hydraulic fluid 13 to flow into the pump 9 as well as through the hydraulic line to the density trap 15 and valve 141 is closed when the pump 9 and hydraulic fluid line 11 are filled. After the dilatometer system 100 is filled with a working fluid and hydraulic fluid, valves 141, 131, and 135 are closed. Three-port valve 137 is closed with respect to the working fluid tank 123 but still allows working fluid 5 to flow between the density trap 15 and the reactor 3.

In operation with the test sample/specimen 17 in place, the processor 151 may interface through a pump controller 153 connected to the pump 9 and a heater controller 155 connected to the heater 149. For example, in an isobaric test the processor 151 will control the pump 9 to create a precise desired pressure within the dilatometer system 100 and then the processor 151 will cause the heater controller 155 to systematically increase/sweep the temperature upward looking for the glass transition temperature, $T_g$, for example. In same configurations, the heater 149 may contain resistive heating elements or inductive heating elements that introduce heat to the reactor 3. Additional embodiments may include heaters that introduce heat to the reactor 3 in other ways as understood by those of ordinary skill in the art.

Using the processor 151, the dilatometer system 100 of FIG. 3 may measure the specific volume and temperature and provide this data in real time. This configuration of a dilatometer system 100 may run isothermal tests, where a temperature is reached at a proscribed heating rate before conducting a pressurization cycle. As mentioned above, the dilatometer system 100 may also be able run isobaric tests to reach a proscribed pressure and then run a thermal cycle. As understood by those of ordinary skill in the art, the system 100 may determine other properties of materials because the system 100 has the ability to run isochoric tests at a constant volume, in which the system 100 heats and pressurizes the test sample 17 in a controlled manner such that the volume of the specimen 17 remains constant. As understood by those of ordinary skill in the art, isochoric test may be useful to find other engineering properties of materials.

In summary, the dilatometer system 1 of FIG. 1 and dilatometer system 100 of FIG. 3 greatly simplifies the operation of prior art dilatometers is the use of two or more immiscible fluids and a density trap 15. Two fluids are useful to conduct the test because the working fluid 5 in the reactor 3, is substantially inert to test sample 17 and may have thermal capability to, for example, at least about 200 degrees Celsius higher than the predicted $T_g$ of sample 17. In other embodiments, the thermal capability of the dilatometer system 1 may be at least about 1000 degrees Celsius. The pressurizing (hydraulic) fluid 13 should be compatible with the pump seals and surfaces. The two fluids are kept physically separated, except for the moving interface formed by the immiscible fluids. Each of the fluids are maintained away from areas that would detract from the operation of the dilatometer system 100. If the pair of immiscible fluids are any suitable hydraulic fluid and Galinstan, a commercially available gallium eutectic, the hydraulic fluid 13 may be kept out of the heating zone and not contact the polymer sample 17. The working fluid 5 should be kept out of the pump 9 for reasons of corrosion and pump durability. The immiscibility of the fluids, and the small interfacial area, keeps the fluids from mixing or combining and the density trap 15 keeps the lighter fluid from "climbing" over the heavier fluid and getting into the reactor 3. The immiscibility of the liquids allow this to be done without the complication of a prior art type of bellows system used to separate and segregate the liquids. The immiscibility of the liquids reduces overall system stiffness and increases the responsiveness of the dilatometer system 100. Further, the dilatometer system according to the present disclosure may provide more repeatable results with enhanced accuracy as compared to conventional dilatometers. Ideally, the working fluid surrounds the test sample 17 in the chamber when it is being tested. Samples that may be tested are polymers and other materials in which changes in volume under one or more pressures and/or temperatures are desired to be known.

Example methods may be better appreciated with reference to flow diagrams. For purposes of simplicity, explanation of the illustrated methodologies are shown and described as a series of blocks. It is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 4:
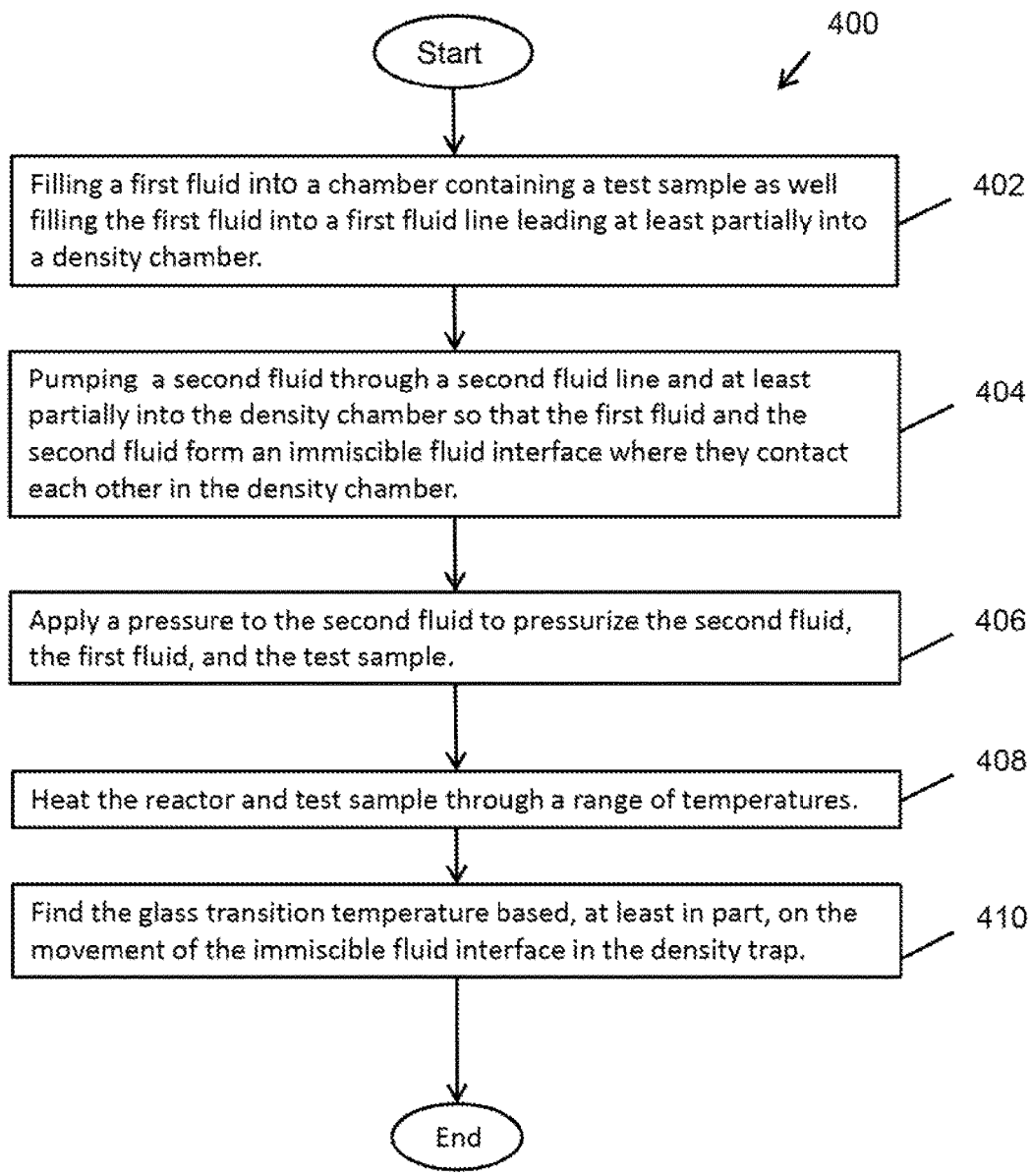
FIG. 4 illustrates an example method of using a pair of immiscible fluids to find characteristics of material such as the glass transition temperature, $T_g$, for example according to one or more embodiments.

FIG. 4 illustrates a method 400 of using two different immiscible fluids in a dilatometer. The method 400 begins by filling a reactor containing a test sample as well as filling a first fluid line leading at least partially into a density trap with a first fluid, at 402. A second fluid is pumped through a second fluid line and at least partially into the density trap, at 404, so that the first fluid and the second fluid contact each other in the density trap and form and immiscible fluid boundary/interface because the first and second fluid pairs are immiscible fluid pairs. A desired pressure is applied to the second fluid, at 406, to pressurize the second fluid, the first fluid, and the test sample. The reactor and test sample are heated, at 408, through a range of temperatures. The glass transition temperature is found, at 410, based, at least in part, on the movement of the immiscible fluid interface in the density trap. In some configurations, the rate of movement of the immiscible fluid interface changes, indicating a rate of change of a specific volume of the test sample, which indicates at what temperature the glass transition temperature, $T_g$, occurs. In other configurations, the first fluid is Galinstan and the second fluid is a hydraulic fluid.

Figure 5:
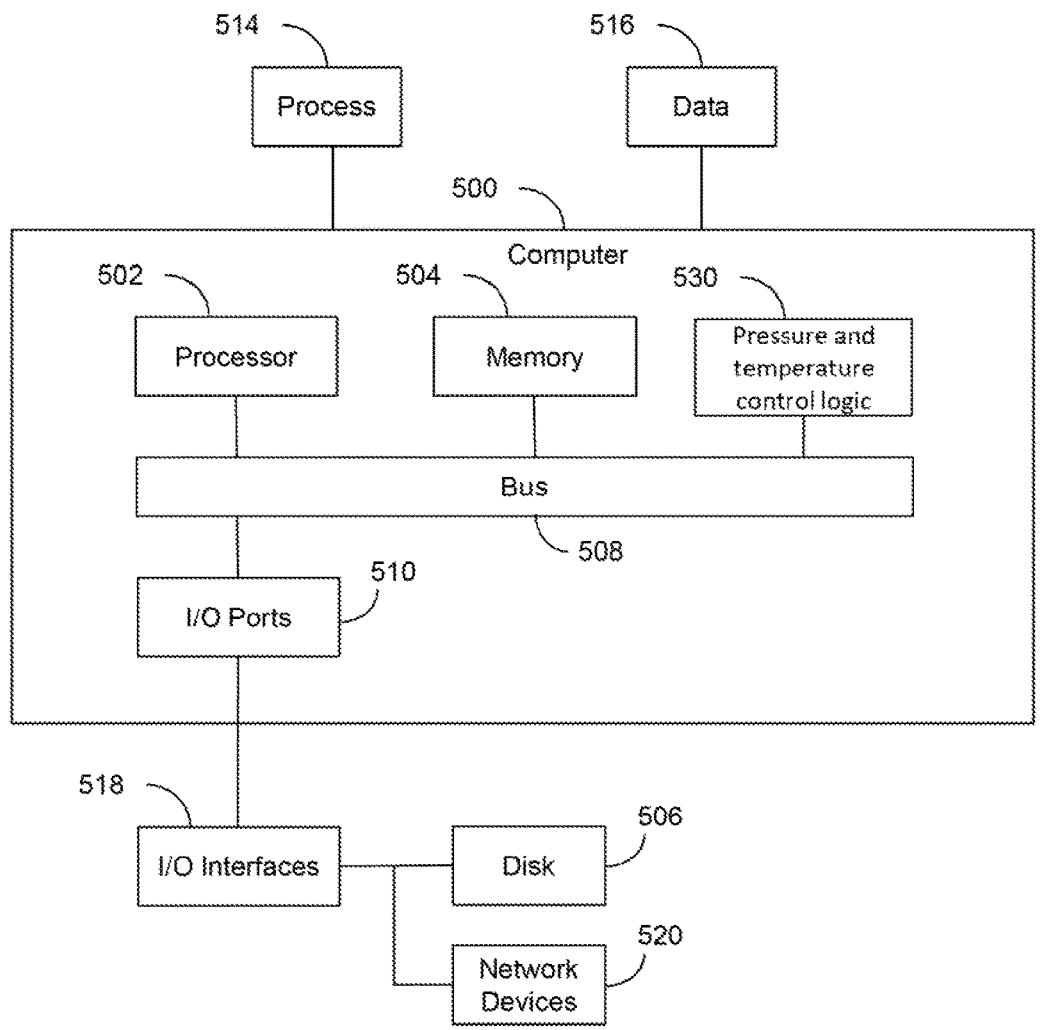
FIG. 5 illustrates an example computer system that may aid in operating a dilatometer system when finding characteristics of a test sample according to one or more embodiments.

FIG. 5 illustrates an example computing device in which at least some portions of example systems and methods described herein, and equivalents, may operate. The example computing device may be a computer 500 that includes a processor 502, a memory 504, and input/output ports 510 operably connected on a bus 508. In one example, the computer 500 may include a pressure and temperature control logic 530 configured to control a pump to pressure a pair of immiscible fluids in a dilatometer as described above and to control the heater associated with a reactor. In some configurations the computer 500 may be able to calculate various parameters of a test sample in a reactor of the dilatometer based, at least in part, on volume changes as indicated by an intersection of a boundary of the two immiscible fluids. In different examples, the pressure and temperature control logic 530 may be implemented in hardware, software, firmware, and/or combinations thereof. Thus, logic 530 may provide means (e.g., hardware, software, firmware) for controlling a dilatometer system with a pair of two immiscible fluids and provide a means of finding one or more parameters of a test sample under test in the dilatometer system. While logic 530 is illustrated as a hardware component attached to bus 508, it is to be appreciated that in one example, logic 530 could be implemented in processor 502.

Generally describing an example configuration of computer 500, processor 502 may be a variety of various processors including dual microprocessor and other multi-processor architectures. Memory 504 may include volatile memory and/or non-volatile memory. Non-volatile memory may include, for example, ROM, PROM, EPROM, and EEPROM, Volatile memory may include, for example, RAM, synchronous RAM (SRAM), dynamic RAM (DRAM), synchronous DRAM (SDRAM), double data rate SDRAM (DDR SDRAM), direct RAM bus RAM (DRRAM) and the like.

A disk 506 may be operably connected to computer 500 via, for example, an input/output interface (e.g., card, device) 518 and an input/output port 510. Disk 506 may be, for example, a magnetic disk drive, a solid state disk drive, a floppy disk drive, a tape drive, a Zip drive, a flash memory card, and/or a memory stick. Furthermore, disk 506 may be a CD-ROM, a CD recordable drive (CD-R drive), a CD rewriteable drive (CD-RW drive), and/or a digital video ROM drive (DVD ROM). Memory 504 can store a process 514 and/or a data 516, for example. Disk 506 and/or memory 504 can store an operating system that controls and allocates resources of computer 500.

Bus 508 may be a single internal bus interconnect architecture and/or other bus or mesh architectures. While a single bus is illustrated, it is to be appreciated that computer 500 may communicate with various devices, logics, and peripherals using other busses (e.g., PCIE, SATA, Infiniband, 1384, USB, Ethernet). Bus 508 can be types including, for example, a memory bus, a memory controller, a peripheral bus, an external bus, a crossbar switch, and/or a local bus.

Computer 500 may interact with input/output devices via input/output interfaces 518 and input/output ports 510. Input/output devices may be, for example, a keyboard, a microphone, a pointing and selection device, cameras, video cards, displays, the disk 506, the network devices 520, and so on. The input/output ports 510 may include, for example, serial ports, parallel ports, USB ports and the like.

The computer 500 can operate in a network environment and thus may be connected to network devices 520 via input/output interfaces 518, and/or the input/output ports 510. Through network devices 520, computer 500 may interact with a network. Through the network, computer 500 may be logically connected to remote computers. Networks with which computer 500 may interact include, but are not limited to, a local area network (LAN), a wide area network (WAN), and other networks. The networks may be wired and/or wireless networks.

In the foregoing description, certain terms have been used for brevity, clearness, and understanding. No unnecessary limitations are to be implied therefrom beyond the requirement of the prior art because such terms are used for descriptive purposes and are intended to be broadly construed. Therefore, the disclosure is not limited to the specific details, the representative embodiments, and illustrative examples shown and described. Thus, this application is intended to embrace alterations, modifications, and variations that fall within the scope of the appended claims.

Moreover, the description and illustration of embodiments according to the disclosure are examples and the disclosure is not limited to the exact details shown or described. References to "the preferred embodiment", "an embodiment", "one example", "an example" and so on, indicate that the embodiment(s) or example(s) so described may include a particular feature, structure, characteristic, property, element, or limitation, but that not every embodiment or example necessarily includes that particular feature, structure, characteristic, property, element, or limitation.

What is claimed is:

1. A dilatometer system for measuring a characteristic of a test sample, comprising:
   a reactor adapted to receive the test sample;
   a density trap in fluid communication with the reactor;
   a first fluid selectively filling the reactor and a portion of the density trap;
   a second fluid selectively filling a portion of the density trap; and
   a heater that selectively heats the first fluid,
   wherein the first fluid and the second fluid are immiscible with one another and selectively form an immiscible fluid boundary in the density trap.

2. The dilatometer system of claim 1, further comprising a pump in fluid communication with the density trap.

3. The dilatometer system of claim 2, wherein the second fluid is positioned to prime the pump.

4. The dilatometer system of claim 2, wherein the pump selectively pressurizes the second fluid directly, wherein the second fluid pressurizes the first fluid and the test sample.

5. The dilatometer system of claim 1, wherein a position of the immiscible fluid boundary within the density trap changes in position based on the characteristic of the test sample.

6. The dilatometer system of claim 1, where the heater is adapted to heat at least the first fluid in the reactor and the test sample over a range of temperatures.

7. The dilatometer system of claim 6, wherein a rate change in the movement of the immiscible fluid boundary over the range of temperatures indicates the glass transition temperature, $T_g$, of the test sample.

8. The dilatometer system of claim 6 further comprising a computer comprising a processor and a memory and having a computer readable instruction set stored in the memory that, when executed by the processor:
   the computer instructs the heater to heat at least the first fluid and the test sample over the range of temperatures; and
   the computer monitors the position of the immiscible fluid boundary over the range of temperatures.

9. The dilatometer system of claim 8, wherein, when the computer readable instruction set is executed by the processor, the computer calculates the glass transition temperature, $T_g$, of the test sample.

10. The dilatometer system of claim 6, wherein:
    the first fluid is a metal or metal alloy that is full liquid over the range of temperatures; and
    the second fluid is a hydraulic fluid.

11. The dilatometer system of claim 10, wherein the first fluid is Galinstan.

12. The dilatometer system of claim 2, further comprising:
    a working fluid tank in fluid communication with the reactor and adapted to selectively store at least some of the first liquid; and
    a hydraulic fluid tank in fluid communication with the pump and adapted to store at least some of the second liquid.

13. The dilatometer system of claim 12, further comprising:
    a first 2-port valve in fluid communication between the hydraulic fluid tank and the pump;
    a second 2-port valve in fluid communication between the pump and a second fluid line;
    a first 3-port value in fluid communication between the working fluid tank, and a portion of a first fluid line connected to the reactor, and another portion of the first fluid line connected to the density trap; and
    a third 2-port valve in fluid communication between the working fluid tank and local atmosphere.

14. The dilatometer system of claim 13, further comprising:
    a computer adapted to control the first 2-port valve, the second 2-port valve when priming the pump, the second fluid line, and the density trap with the second fluid when initializing the dilatometer system;
    wherein the computer is adapted to control the first 3-port valve, and the third 2-port valve when filling the first fluid into the first fluid line, the density trap, and the reactor when initializing the dilatometer system;
    wherein the computer is adapted to control the first 2-port valve, the second 2-port valve when removing the second fluid from the pump, the second fluid line, and the density trap when shutting down the dilatometer system; and
    wherein the computer is adapted to control the first 3-port valve, and the third 2-port valve when removing the first fluid from the first fluid line, the density trap, and the reactor when shutting down the dilatometer system.

15. The dilatometer system of claim 14, further comprising:

an argon tank connected between the working fluid tank and the reactor with a second 3-port valve, wherein the computer is adapted to control the second 3-port valve so that argon in the argon tank will assist in filling the first fluid into the first fluid line, the density trap, and the reactor when initializing the dilatometer system, and wherein the computer is adapted to control the second 3-port valve so that argon in the argon tank will assist in removing the first fluid from the first fluid line, the density trap, and the reactor when shutting down the dilatometer system.

16. The dilatometer system of claim 2, wherein the pump is a syringe pump.

17. The dilatometer system of claim 1, wherein the density trap is a P-type of trap.

18. The dilatometer system of claim 2, further comprising:
- a pressure measurement device for sensing the pressure of the fluid exiting the pump;
- a pressure measurement device for sensing the pressure of the first fluid inside the reactor; and
- a temperature measurement device for sensing the temperature of the first fluid inside the reactor.

19. A dilatometer system for measuring a characteristic of a test sample, comprising:
- a reactor adapted to receive the test sample;
- a first fluid selectively filling the reactor;
- a second fluid that is immiscible with the first fluid, the second fluid forming an immiscible fluid boundary at a location where the first fluid contacts the second fluid;
- a heater that selectively heats the first fluid; and
- a computer comprising a processor and a memory and having a computer readable instruction set stored in the memory that, when executed by the processor:
- the computer instructs the heater to heat at least the first fluid and the test sample over a range of temperatures; and
- the computer monitors a volume of the first fluid based on the position of the immiscible fluid boundary over the range of temperatures.

20. The dilatometer system of claim 19, wherein, when the computer readable instruction set is executed by the processor, the computer calculates the glass transition temperature, $T_g$, of the test sample.

* * * * *